(12) United States Patent  
Hairston et al.

(10) Patent No.: US 11,511,149 B2
(45) Date of Patent: Nov. 29, 2022

(54) DEVICE FOR REDUCING ANTERIOR PELVIC TILT AND A METHOD FOR ITS USE

(71) Applicants: Malcolm Hairston, Lower Gwynedd, PA (US); Kim Hairston, Ambler, PA (US)

(72) Inventors: Malcolm Hairston, Lower Gwynedd, PA (US); Kim Hairston, Ambler, PA (US)

( * ) Notice: Subject to any disclaimer, the term of this patent is extended or adjusted under 35 U.S.C. 154(b) by 0 days.

(21) Appl. No.: 16/582,963

(22) Filed: Sep. 25, 2019

(65) Prior Publication Data

US 2021/0086019 A1    Mar. 25, 2021

(51) Int. Cl.
*A63B 21/00* (2006.01)
*A63B 21/065* (2006.01)
*A63B 23/04* (2006.01)
*A61F 5/02* (2006.01)

(52) U.S. Cl.
CPC .......... *A63B 21/4009* (2015.10); *A61F 5/028* (2013.01); *A63B 21/065* (2013.01); *A63B 21/151* (2013.01); *A63B 23/0482* (2013.01)

(58) Field of Classification Search
CPC ..... A63B 23/00; A63B 23/02; A63B 23/0205; A63B 23/0216; A63B 23/0233; A63B 21/0004; A63B 21/00178; A63B 21/06; A63B 21/062; A63B 21/15; A63B 21/151; A63B 21/159; A63B 21/4009; A63B 26/003; A63B 2026/006; A61H 2205/08; A61H 2205/085; A61H 1/00; A61H 1/02; A61H 1/0244; A61H 1/029; A61H 2001/0203; A61F 5/024; A61F 5/026; A61F 5/028
See application file for complete search history.

(56) References Cited

U.S. PATENT DOCUMENTS

| | | | | |
|---|---|---|---|---|
| 5,950,570 A | * | 9/1999 | Dickerson | A01K 25/00 119/792 |
| 6,113,564 A | * | 9/2000 | McGuire | A61H 1/0229 482/131 |
| 8,944,977 B2 | | 2/2015 | Foster | |
| 10,441,001 B1 | * | 10/2019 | Chase | A41B 9/04 |
| 2005/0283104 A1 | | 12/2005 | Abelbeck | |
| 2007/0161473 A1 | * | 7/2007 | McBride | A63B 21/065 482/105 |

(Continued)

OTHER PUBLICATIONS

Author Unknown, 5 Steps for Dealing with Anterior Pelvic Tilt, http://www.theptdc.com/wp-content/uploads/2015/11/5-Steps-for-Dealing-With-Anterior-Pelvic-Tilt.pdf, appeared online before filing date of this application.

*Primary Examiner* — Nyca T Nguyen
*Assistant Examiner* — Zachary T Moore
(74) *Attorney, Agent, or Firm* — Muskin and Farmer LLC (57) ABSTRACT

An exercise device and a method for its use to aid in the correction of Anterior pelvic tilt. A base has an upper support and a lower support. The base device is strapped around a user's stomach and connected to a rope. The rope passes through the user's legs and is attached to a weight holder behind the user. As the user walks forward, the weight holder is dragged along the floor and the force of the weights on the weight holder pressed the base against the user's stomach and aids in proper alignment of the pelvic region.

7 Claims, 10 Drawing Sheets

(56) References Cited

U.S. PATENT DOCUMENTS

| | | | | |
|---|---|---|---|---|
| 2008/0096744 | A1* | 4/2008 | Perry | A61H 1/0292 |
| | | | | 482/144 |
| 2010/0204014 | A1* | 8/2010 | Hoffman | A63B 21/055 |
| | | | | 482/8 |
| 2011/0230314 | A1* | 9/2011 | Hoffman | A63B 24/0062 |
| | | | | 482/51 |
| 2015/0126344 | A1* | 5/2015 | Wehrell | A63B 24/0087 |
| | | | | 482/128 |
| 2017/0189758 | A1* | 7/2017 | Angulo | A63B 21/16 |
| 2017/0312569 | A1* | 11/2017 | Fano | A61H 1/008 |
| 2018/0085618 | A1* | 3/2018 | Cummings | A63B 21/0557 |
| 2018/0311522 | A1* | 11/2018 | Schmidt | A63B 21/06 |
| 2020/0230462 | A1* | 7/2020 | McKeever | A61H 1/0296 |

* cited by examiner

DEVICE FOR REDUCING ANTERIOR PELVIC TILT AND A METHOD FOR ITS USE

BACKGROUND OF THE INVENTION

Field of the Invention

The present general inventive concept is directed to a method and apparatus directed to an exercise device intended to help anterior pelvic tilt.

Description of the Related Art

Figure 1:
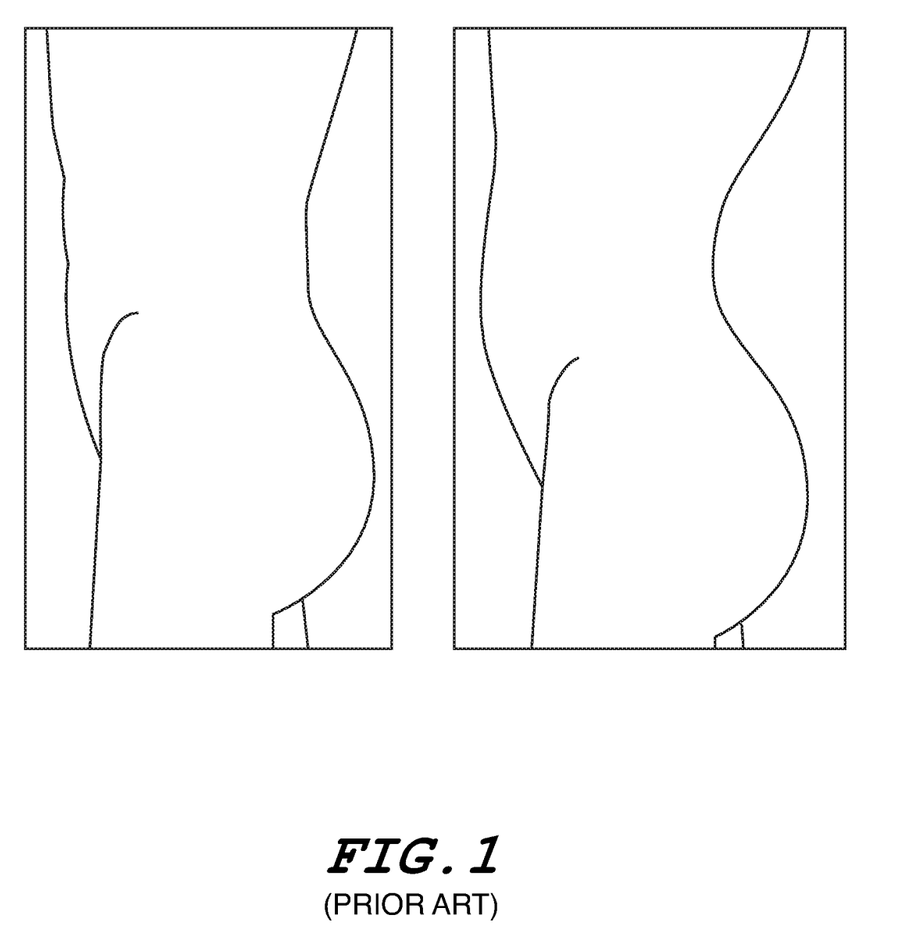
FIG. 1 is a drawing showing a person with normal posture and one with Anterior pelvic tilt, as known in the prior art.

Anterior Pelvic tilt is a common medical condition in which the pelvic tilts towards the front of the body. In FIG. 1, the left drawing shows a normal posture while the right drawing shows anterior pelvic tilt. Anterior pelvic tilt can lead to numerous medical issues, including poor posture, chronic back pain, increased pressure on the spinal vertebrae, hip knee and ankle dysfunction, hernias and others. Anterior pelvic tilt can have numerous causes, such as sitting incorrectly for a long period of time.

There are various exercises designed for addressing anterior pelvic tilt, but these usually involve sitting or lying on the floor or standing in one location rather than being up and actually moving around. Skills learned while standing still, sitting or lying down may not translate well into dynamic movement because all of the same muscles are not being utilized the same in each instance. Some exercises that can be used to help correct anterior pelvic tilt are squats and stretches.

What is needed is an improved way to correct Anterior pelvic tilt.

SUMMARY OF THE INVENTION

It is an aspect of the present invention to provide an improved device to assist in correcting anterior pelvic tilt and other conditions.

These together with other aspects and advantages which will be subsequently apparent, reside in the details of construction and operation as more fully hereinafter described and claimed, reference being had to the accompanying drawings forming a part hereof, wherein like numerals refer to like parts throughout.

BRIEF DESCRIPTION OF THE DRAWINGS

Further features and advantages of the present invention, as well as the structure and operation of various embodiments of the present invention, will become apparent and more readily appreciated from the following description of the preferred embodiments, taken in conjunction with the accompanying drawings of which.

DESCRIPTION OF THE PREFERRED EMBODIMENTS

Reference will now be made in detail to the presently preferred embodiments of the invention, examples of which are illustrated in the accompanying drawings, wherein like reference numerals refer to like elements throughout.

The general inventive concept relates to a physical exercise device used to help correct Anterior pelvic tilt and a method for using the physical exercise device. The device is generally paddle shaped and is strapped around a person's waist and stomach. A handle on the device is attached to a rope which runs behind the person's legs and is attached to weights on a sled (cart, or another device that can be pulled). The person would then walk forward while pulling the weight behind him/her. The weight would cause the device to press against the person's pelvic area which would initially cause even more anterior pelvic tilt, however a person's natural reaction to the increased pressure in the pelvic area would then be to compensate for this additional pelvic pressure thereby causing the person to walk in a more upright fashion which would counteract the effect of the anterior pelvic tilt. Thus, when a person walks utilizing the present device (which would initially cause an increase is anterior pelvic tilt), the person would naturally adjust his/her walk in order to compensate for the increased anterior pelvic tilt, thereby training the person to improve his/her posture.

The device fits flatly against the anterior torso, being anchored to the torso with belts or straps. The device at its inferior end presses against the left and right superior ramus of the pelvic girdle, while the middle and superior portion presses against the lower and middle abdomen. The bottom of the device has a protrusion that extends downward below the crotch and which allows for the attachment of a rope, strap or chain which in turn is secured to some type of weighted object. The device causes the pelvic girdle of the user to rotate anteriorly as the user ambulates in a forward direction. The user must produce a counter force against the anterior rotational forces by using the appropriate lumbar/pelvic/core muscles ("Lumbo-Pelvic-Hip Complex) to rotate the pelvic girdle back posteriorly. The device provides the user proprioceptive input while in active movement in order to train the user to easily activate the appropriate muscles to maintain pelvic and spinal alignment while sitting, standing, walking or running. The present device produces superior physiological results during physical exercise for athletic training, fitness maintenance, and physical therapy and rehabilitation in a cost effective and time efficient manner.

Figures 2, 3:
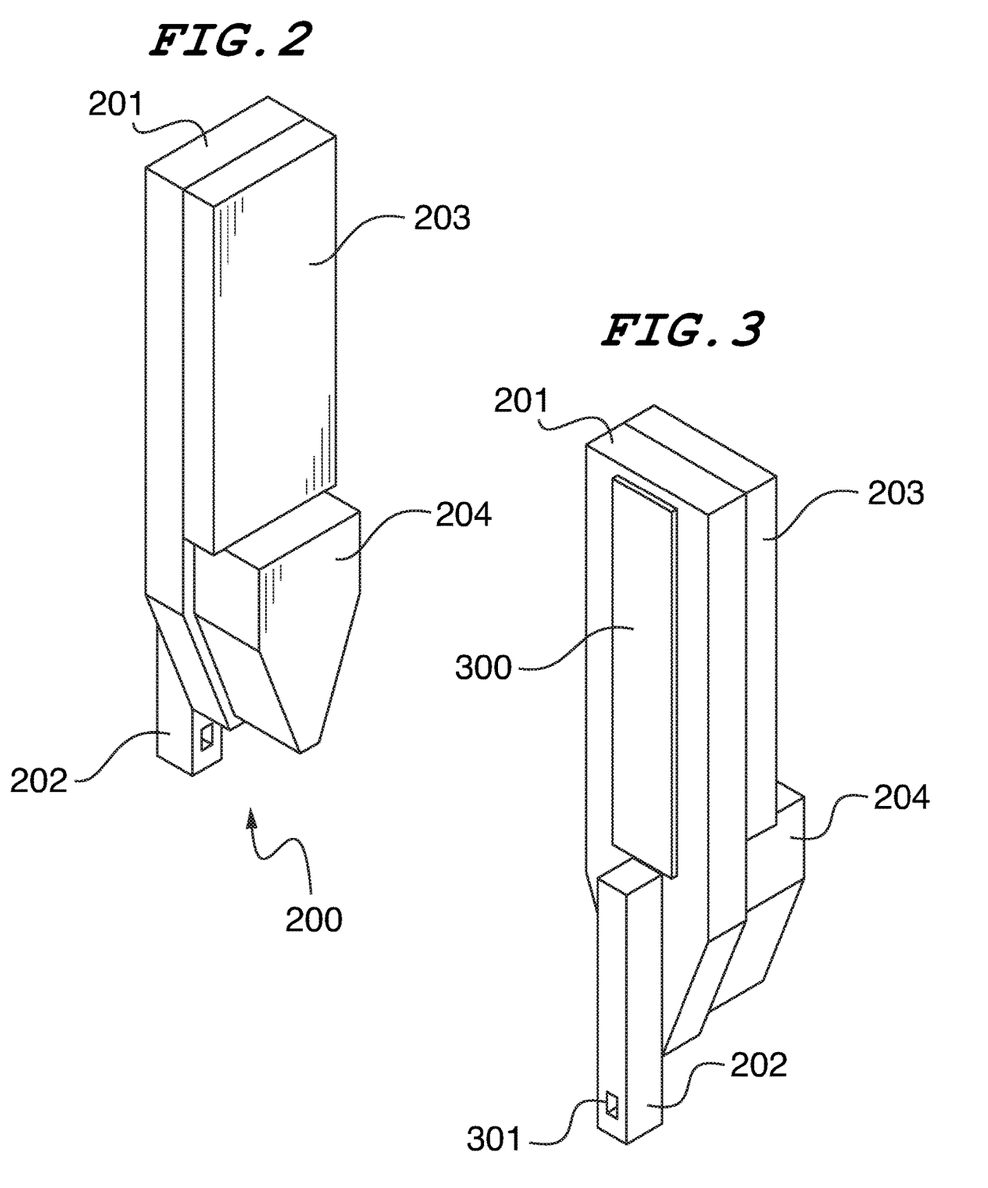
FIG. 2 is a drawing of a diagonal rear view of an exercise device, according to an embodiment.
FIG. 3 is a drawing of a diagonal front view of the exercise device, according to an embodiment.

FIG. 2 is a drawing of a diagonal rear view of an exercise device, according to an embodiment.

A base 201 is rectangular shaped with a trapezoid shape on the bottom (although it can be any other shape as well). A handle 202 is attached to the base 201. An upper support 203 is attached to the base 201. A lower support 204 is also attached to the base 201. An edge of the lower support 204 abuts an edge of the upper support 203, with the lower support 204 being wider so that the lower support 204 extends past the upper support 203.

Note that the upper support 203 matches the height and length of its corresponding portion of the base 201. The lower support 204 has a smaller outline than its corresponding portion of the base 201 as shown in FIG. 1 (this is more clearly shown in FIG. 5).

Note that all parts can be made of any suitable material, such as wood, hard plastic, foam, pvc, etc. All of the parts do not need to be made out of the same material and any combination of materials can be used for the parts. In one embodiment, the base 201 and handle 202 are made out of wood (or other hard material). The upper support 203 and the lower support 204 can be made out of foam (or other slightly softer material) which would be more comfortable pressing against the user's body but would still not lose its shape.

All parts can be attached by any permanent method, such as glue (or other adhesive), nails, screws, etc.

FIG. 3 is a drawing of a diagonal front view of the exercise device, according to an embodiment.

An abrasive surface 300 (e.g., sandpaper, hook and loop fastener or other such rough surface) is attached to a front of the base 301. The abrasive surface can be attached to the front of the base 101 using glue or other attachment mechanism. The abrasive surface 300 is used to receive a strap 800, 801 which are both wrapped around the abrasive surface (see FIG. 8) so that the strap would not slide (in any direction). If the abrasive surface 300 is a hook and loop fastener (e.g., VELCRO), then both of the straps 800, 801 (each of the straps in its entirety (including both sides) or just a portion of them (including both sides)) would be made of the cooperating (to the material used on the abrasive surface 300) hook/loop fastener (e.g., VELCRO) so that the straps would stick on the abrasive surface 300. It is important that the strap be secure against the device so that there is no slippage.

A hole 301 in the handle 302 is used to receive a clip (e.g., a carabiner clip or other type of clip) which is used to connect a rope to the handle 202.

Figure 4:
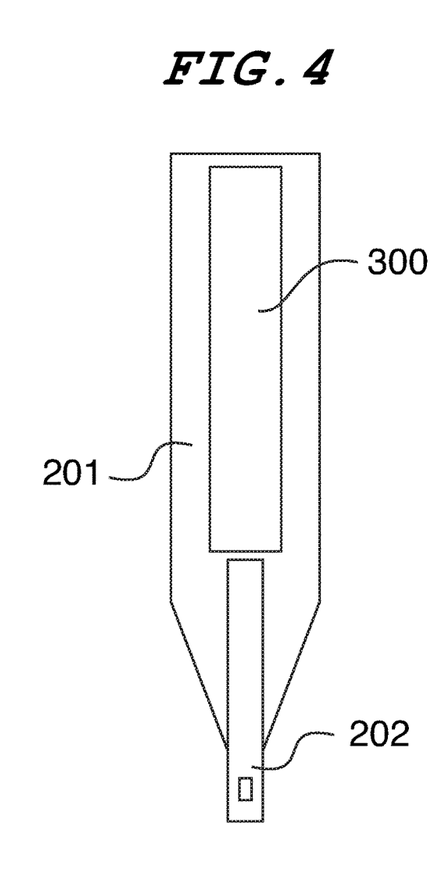
FIG. 4 is a drawing of a front view of the exercise device, according to an embodiment.

FIG. 4 is a drawing of a front view of the exercise device, according to an embodiment.

There is a slight gap between the abrasive surface 300 and the handle 202 (although this is not required).

Figure 5:
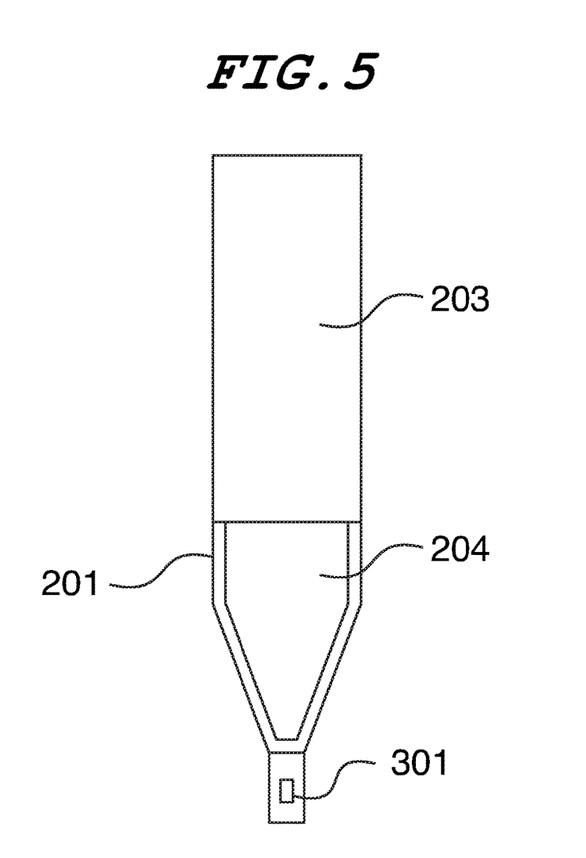
FIG. 5 is a drawing of a rear view of the exercise device, according to an embodiment.

FIG. 5 is a drawing of a rear view of the exercise device, according to an embodiment.

Note that there is extra space on the outline around the lower support 204, in other words the base 201 is slightly larger all around the lower support 204.

Figure 6:
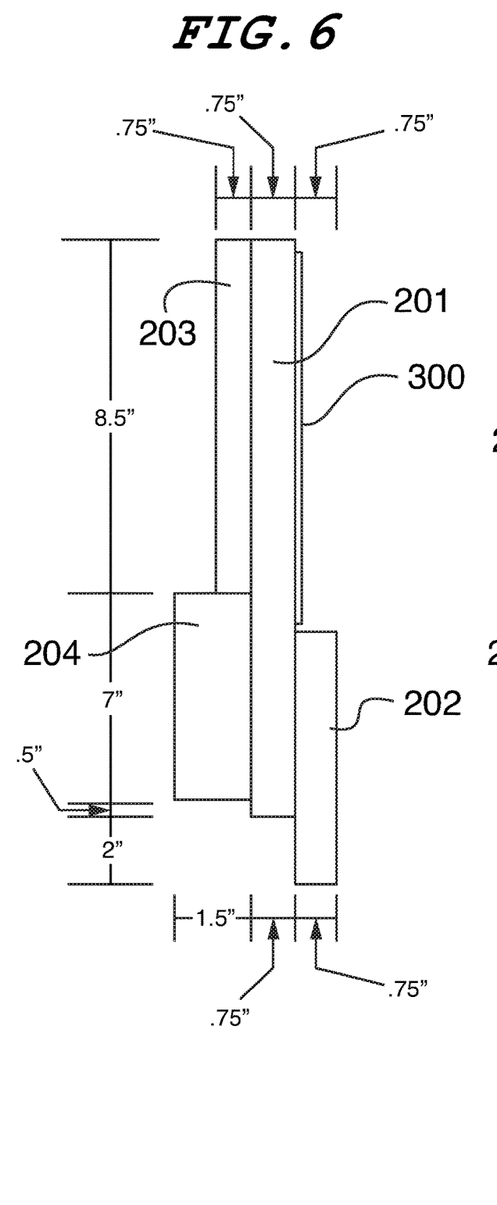
FIG. 6 is a drawing of a side view of the exercise device with sample dimensions, according to an embodiment.

FIG. 6 is a drawing of a side view of the exercise device with sample dimensions, according to an embodiment.

Note that the width of the lower support 204 is wider than the upper support 203 thereby providing extra space (thickness) to the lower support 204 relative to the upper support 203. This extra width provides a gap between the upper support 203 and the person's stomach thereby causing the lower support 204 to press against the user's pelvic area with more pressure then the upper support 203 would press against the user's stomach, thereby "encouraging" anterior pelvic tilt which would typically cause a compensation reaction in the user.

Note that the width of the lower support 204 is 1.5 inches (or 2.25 inches if you count the base 201) and the width of the upper support 203 is 0.75 inches (or 1.5 inches if you count the base 201). Thus, the difference in net width between the lower support 204 and the upper support 203 is 0.75 inches, although this difference can be other amounts as well, for example at least 0.25 inches, at least 0.50 inches, or ranging from 0.25 inches (inclusive) to 1 inch (inclusive), or ranging from 0.25 inches (inclusive) to 5 inches (inclusive), etc.

Figure 7:
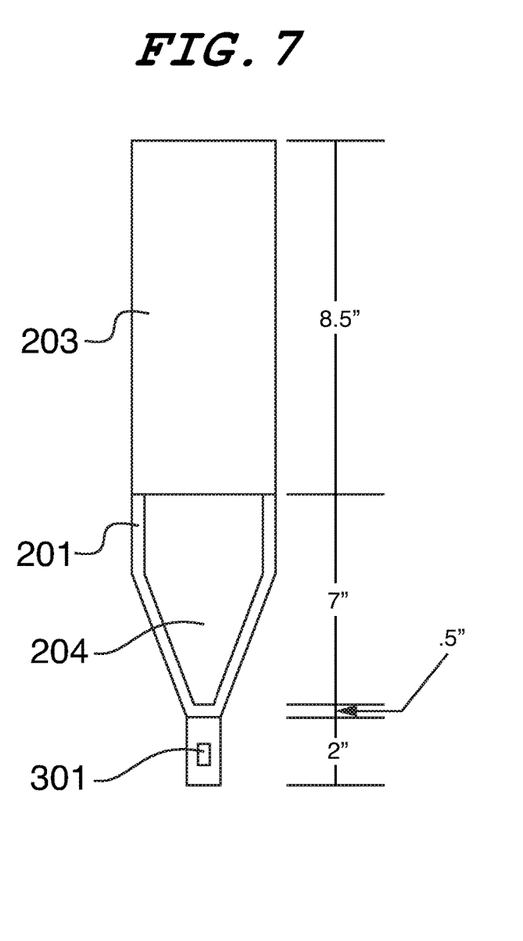
FIG. 7 is a drawing of a rear view of the exercise device with sample dimensions, according to an embodiment.

FIG. 7 is a drawing of a rear view of the exercise device with sample dimensions, according to an embodiment. More dimensions (measurements) are shown. Note that the dimensions (measurements) shown in FIGS. 6-7 are just one example, and it can be appreciated that other sizes and ratios of parts can be used as well.

Note that all differences sizes of parts (or particular lengths of parts or extending lengths) shown herein are not limited to the exact difference in size shown but can for example be in a range from 25% (inclusive or not inclusive) to 200% (inclusive or not inclusive) of the different in size shown. For example, the length of a portion of the handle 202 which extends past the base 201 is two inches (as shown in FIG. 6). However, this length (or any measurement, size, difference in measurements, described or shown herein) can be anywhere from 25% to 200% of the shown length/value (e.g., two inches) which would be 0.5 inches (inclusive) to four inches (inclusive). In another embodiment, the length in question can be at least (or greater than) 25% of the shown length (e.g., at least 0.5 inch). In another embodiment, the length in question can be smaller than (or at most) 200% of the shown length (e.g., less than 2 inches). In another embodiment, any lengths/sizes can be in a range from 25% (inclusive or not inclusive) to 200% (inclusive or not inclusive) of the shown length. In another embodiment, such length can be at least (or greater than) the shown value, in a further embodiment, such length can be at most (or less than) the shown value. These limits can apply to any length, measurement, size, difference, etc. In a further embodiment, the length (any length) can be outside of this range as well and hence the invention is not necessarily limited to any such range, value or limitation. All ranges and inequalities can be inclusive or not inclusive (e.g., any of greater than, greater than or equal to, less than, less than or equal to).

Figure 8:
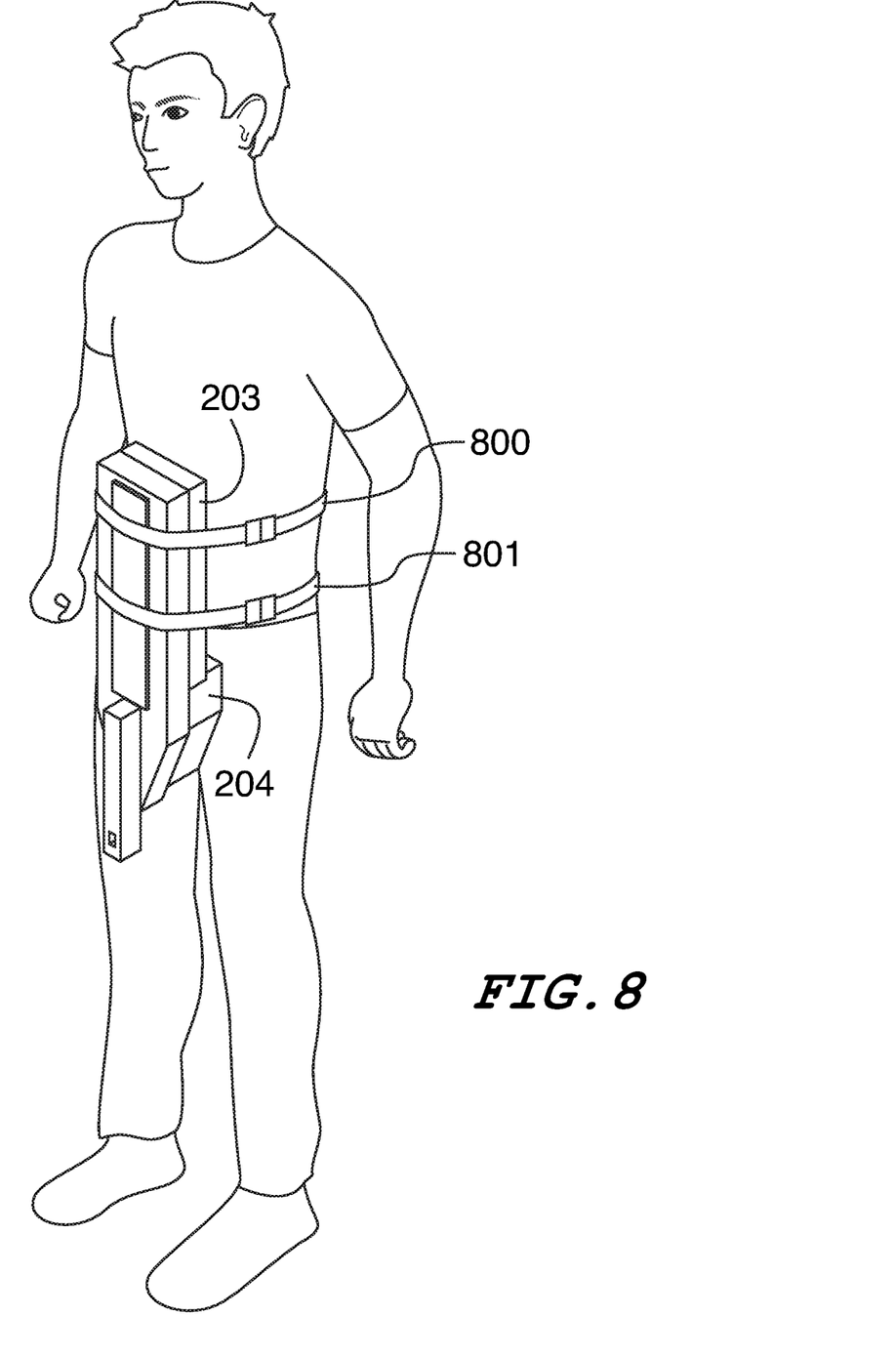
FIG. 8 is a drawing of a person with the exercise device strapped on a person, according to an embodiment.

FIG. 8 is a drawing of a person with the exercise device strapped on a person, according to an embodiment.

A top strap 800 wraps (and is tightened) around the persons T spine (which stabilizes the lower spinal column). When something is pushing against the pelvic area/bone the user would feel his/her entire torso tilting so he/she would naturally try to stand up (compensate) against that force. A bottom strap 801 wraps and is tightened) around the person's waist.

Each strap 800, 801 (can also be referred to as belts) can have a ratchet, buckle, or other tightening device. The upper support 203 is positioned over the user's stomach while the lower support 204 is positioned over the user's pelvic area. Because the lower support 204 is wider, the lower support presses against the user's pelvic area while the upper support 203 has a little more room between the upper support 203 and the user's stomach. Note that the lower support 203 has a tapered shape which gets smaller towards the downward direction which gives the user more room near his/her legs (leg room) to walk. Both straps 800, 801 should be tightened when placed around the user so they should rest tightly but not so tight as to be uncomfortable. The user can strap the device onto himself/herself standing up or sitting down (which may be easier).

Note that the handle 202 sticks out (as shown in FIG. 6) two inches (or more) below the lower support 204 with the hole 301 extending at least another 1.5 inches past the end of the base 201. For example, the hole can be 0.25 inch square (or other size) and can be one inch (or less) from a bottom of the handle 202 (the bottom being in a direction away from the upper support 203), or at least 1.5 inches away from a bottom of the base 201). The hole 301 should preferably (but not required) be in the lower portion of the handle 202 (lower meaning in a direction away from the upper support 203). The hole being below the base 201 provides leverage as the lower it is (relative to the lower support 204) the more force weights (shown in FIG. 9) would exert against the user's pubic bone.

Figure 9:
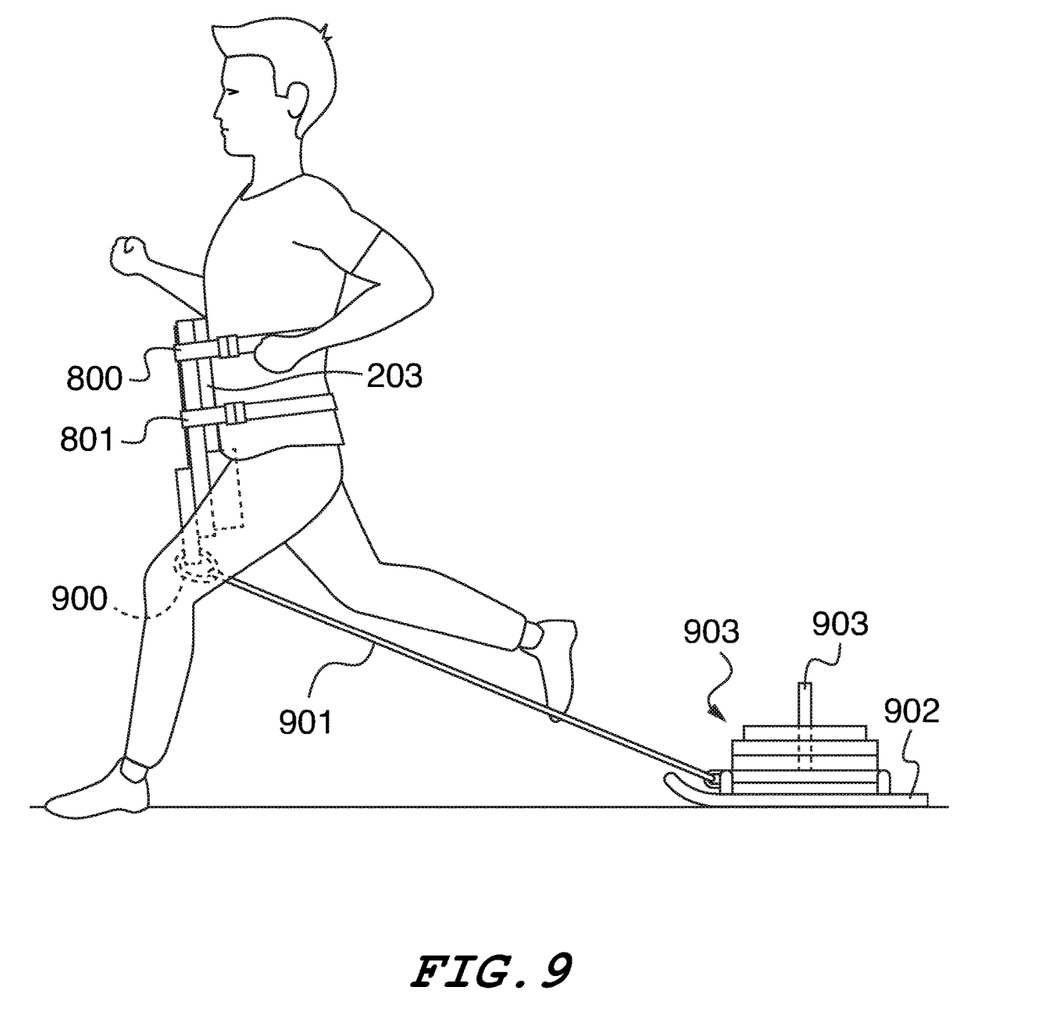
FIG. 9 is a drawing of the person utilizing the exercise device to pull weights behind him/her, according to an embodiment.

FIG. 9 is a drawing of the person utilizing the exercise device to pull weights behind him/her, according to an embodiment.

A rope 901 (or pulley, etc.) is connected to a clip 900 (e.g., a carabiner clip or other type of clip) which clips into/through the hole 201. An opposite end of the rope 901 is connected to a weight holder 902 (e.g., a sled or other movable object such as a cart, pallet, etc.) The weight holder can have a vertical pole 903 to which round weights 904 can be placed thereon, although any type of weights can be placed on the weight holder.

Once the device is attached to the user as shown and the device is also attached to the weight holder as shown, then the user should walk forward. As the user walks forward, he/she will drag the weight holder along the ground. The force of the weights behind the user pulls the user's pelvic area behind him/her which would initially cause even more anterior pelvic tilt (the user would feel his/her entire torso tilt). The user would have a natural inclination to counter this force by standing up against that tilt (and pushing against the lower support 204) thereby walking in a more upright position to compensate for the exaggerated anterior pelvic tilt caused by the device. This compensation would train the user to walk in a more upright fashion and strengthen/activate the proper muscles which aid in walking in a more upright fashion (some of which may usually be inactive. Thus, the device as used herein would help (to activate and strengthen) certain muscles which would help the user overcome anterior pelvic tilt.

Note that the lower support 204 is wider than the upper support 203 (as discussed above and shown in FIG. 6). If the entire device were flat then the lower support 204 would not exert as much pressure against the user's pubic bone in relation to the stomach (the pubic bone is typically further back from the stomach)

Thus, the device when used as shown helps the user learn to use muscles required to walk in the upright (non-anterior pelvic tilt) position. Without such a device, someone with anterior pelvic tilt will continue to walk in the tilted position without strengthening the muscles required to walk more upright.

The user can experiment with different amounts of weights until the ideal amount of weight is utilized to assist in the proper alignment of the pelvic region while not being too heavy to prevent the user from walking properly. Typically, the ideal weight would be 20 pounds but can ideally be in the range from 10 to 20 pounds. The weight should be heavy enough so that the lower support 204 pushes against the pelvic bone but not so heavy that the user would start to compensate with abdominal muscles.

Figure 10:
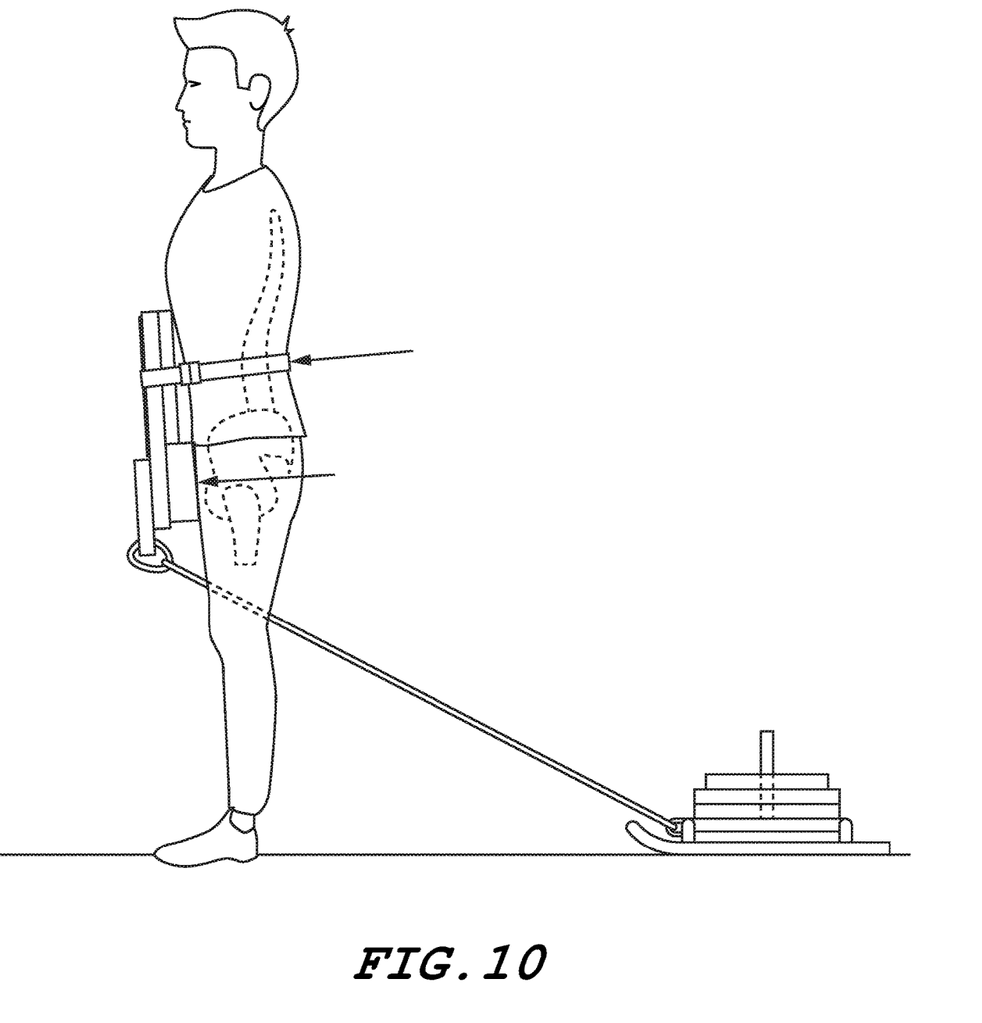
FIG. 10 is a drawing showing critical leverage points, according to an embodiment.

FIG. 10 is a drawing showing critical leverage points, according to an embodiment.

The device creates two critical leverage points. One (the higher one shown in FIG. 10) along the torso and the lumbar spine in the rear. The second (the lower one shown in FIG. 10) is against the pubic bones in the front of the person/user/

Figure 11:
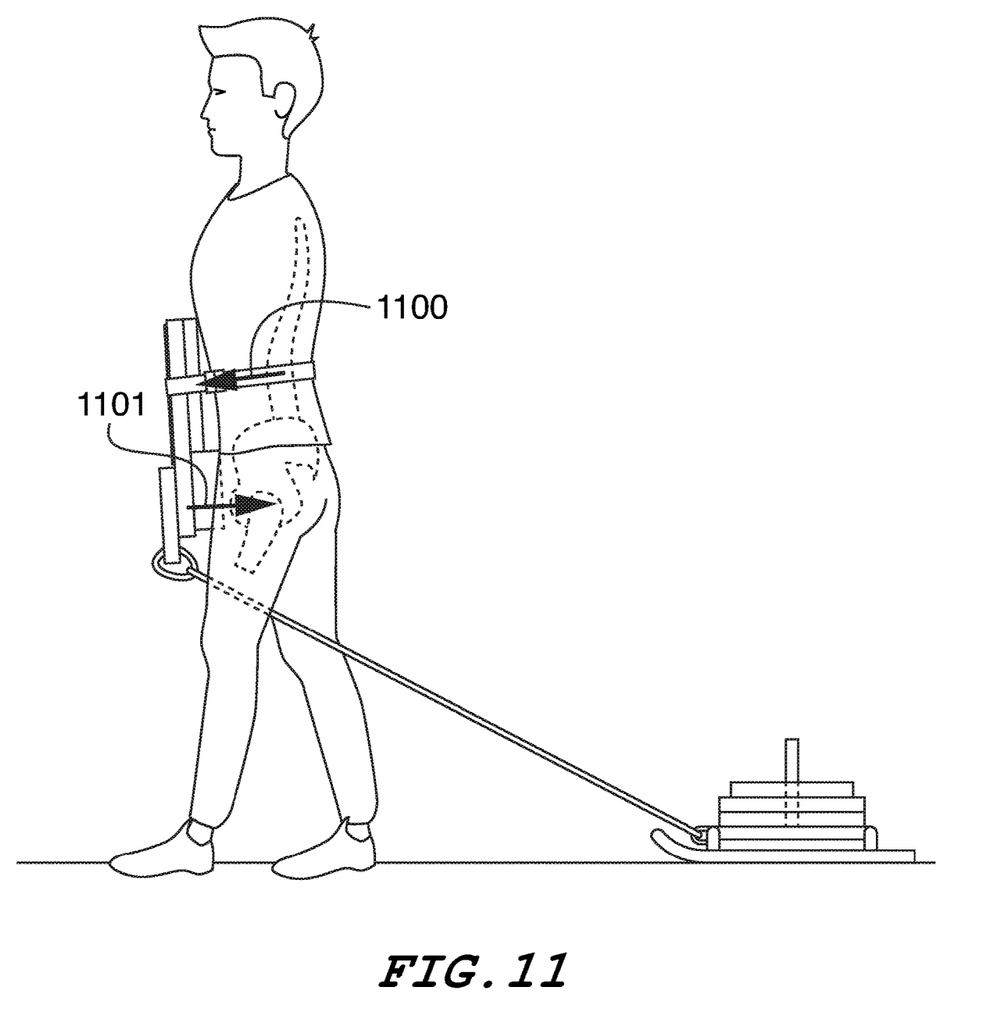
FIG. 11 is a drawing showing forces created when utilizing the present inventive concept.

FIG. 11 is a drawing showing forces created when utilizing the present inventive concept.

As the user walks forward, the device will simultaneously press against the pubic bones (arrow 1101) pushing them back, while also pressing against the lumbar spine (arrow 1100) pulling it forward. The two opposing forces would have the net effect of tilting the lower torso forward.

Figure 12:
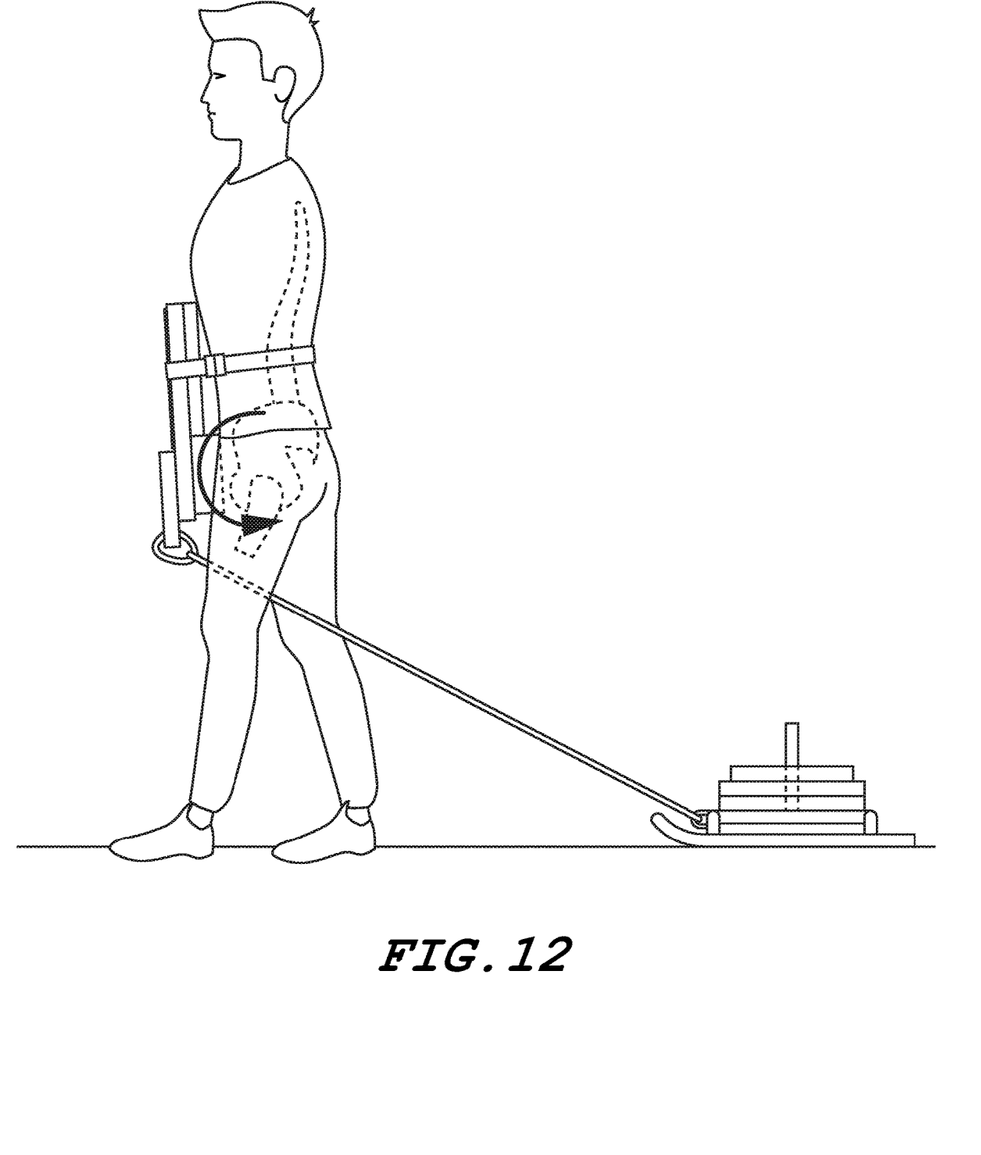
FIG. 12 is a drawing showing rotational force into an anterior pelvic tilt, according to an embodiment.

FIG. 12 is a drawing showing rotational force into an anterior pelvic tilt, according to an embodiment.

The two opposing forces which tilt the torso forward will cause the pelvic girdle to rotate forward into an anterior pelvic tilt, as shown in FIG. 12.

Figure 13:
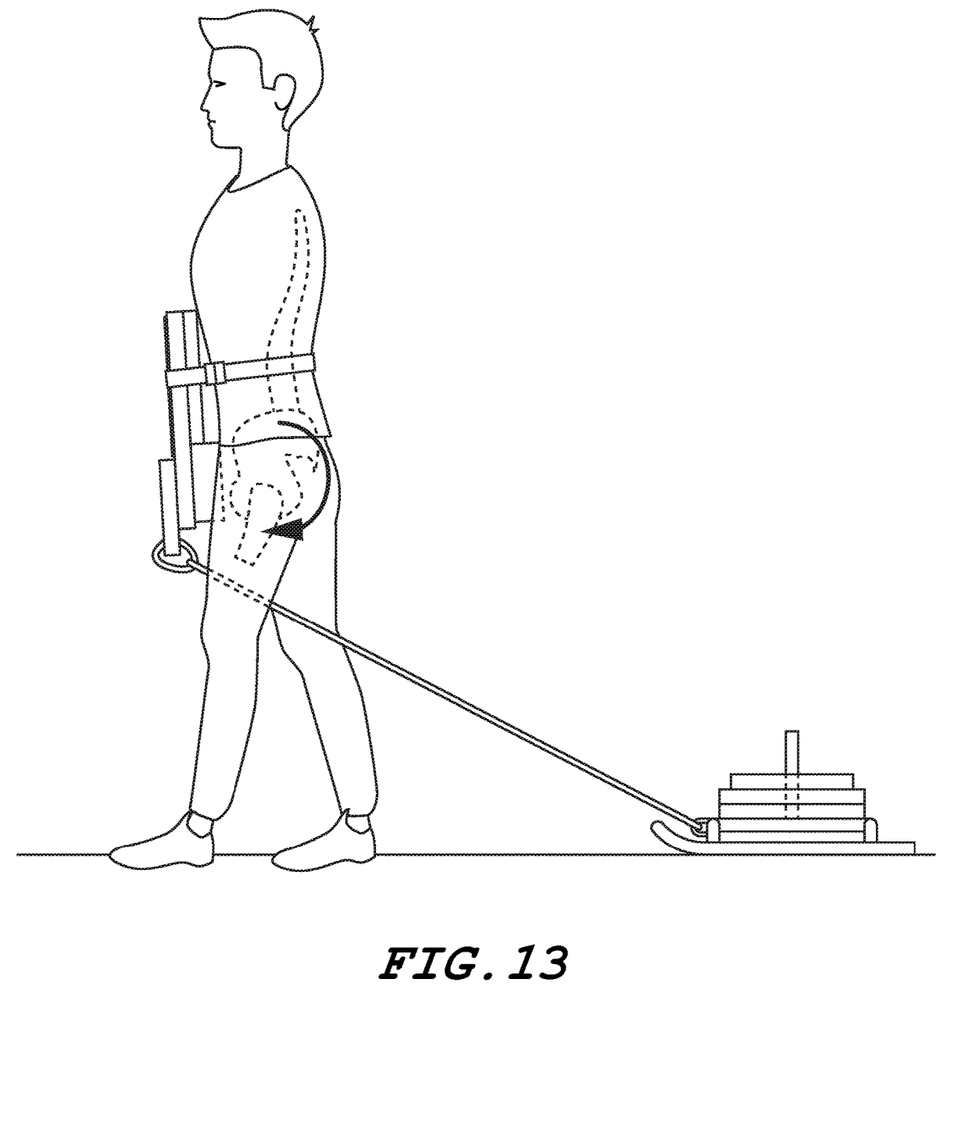
FIG. 13 is a drawing showing a compensatory rotation correcting the anterior pelvic tilt, according to an embodiment.

FIG. 13 is a drawing showing a compensatory rotation correcting the anterior pelvic tilt, according to an embodiment.

The user would use the pubic bones as a pivot point and would counter the rotation force (shown in FIG. 12) against the lower portion of the device with an opposite rotational force (shown in FIG. 13). This would have the effect of rotating the pelvic girdle posteriorly, bringing the device (the base 201) perpendicular to the ground. Hence, the device is activating/strengthening muscles that enable the posterior rotation (shown in FIG. 13), which help train the user to walk more upright. Usage of the device over time would thus help/train the user to compensate for his/her anterior pelvic tilt and walk more upright.

Note that the shapes and dimensions described and illustrated herein are one embodiment of the inventive concept, and it can be appreciated that the invention can be constructed using structures of different dimensions and/or shapes. Each individual part, or combination of parts, can be made using different shapes than what is described/illustrated herein, for example the base (and/or upper support) can be ovular instead of rectangular, etc. Changes in shape/structure can be major (different shapes altogether than what is illustrated/described herein) or minor (using rounded edges instead of right angles for any edge such as on the base 201 (or any other part), etc.

The many features and advantages of the invention are apparent from the detailed specification and, thus, it is intended by the appended claims to cover all such features and advantages of the invention that fall within the true spirit and scope of the invention. Further, since numerous modifications and changes will readily occur to those skilled in the art, it is not desired to limit the invention to the exact construction and operation illustrated and described, and accordingly all suitable modifications and equivalents may be resorted to, falling within the scope of the invention.

What is claimed is:

1. A method, comprising:
providing: a base with a flat front surface, an upper support with a flat back surface and a flat lower surface, the upper support attached to the base, the flat back surface of the upper support abutting the flat front surface of the base, a lower support with a flat back surface and a flat upper surface, the lower support attached to the base, the flat back surface of the lower support abutting the flat front surface of the base, the flat lower surface of the upper support abutting the flat upper surface of the lower support and an elongated handle attached to the base, the handle comprising a hole located at a first end of the handle, the first end of the handle positioned away from the upper support;

strapping the base to a user's waist using a first strap;

attaching the hole to a first end of a rope, a second end of the rope opposite to the first end attached to a weight holder behind the user, the weight holder comprising weights, the rope passing between the user's legs; and the user walking forward.

2. The method as recited in claim 1, further comprising strapping a second strap around the base and the user's stomach and back.

3. The method as recited in claim 1, further comprising, as the user walks forward, force from the weights pulls behind on the user's pelvic region.

4. The method as recited in claim 1, further comprising providing an abrasive surface on a front of the base, wherein the first strap passes around the abrasive surface.

5. The method as recited in claim 1, wherein the lower support has a greater width than the upper support.

6. The method as recited in claim 1, wherein the upper support is rectangular shaped.

7. The method as recited in claim 1, wherein the providing further provides that the lower support is tapered which gets narrow towards an end of the lower support.

\* \* \* \* \*